United States Patent [19]

Palepu et al.

[11] Patent Number: 5,066,647
[45] Date of Patent: Nov. 19, 1991

[54] CYCLOPHOSPHAMIDE - ALANINE LYOPHILIZATES

[75] Inventors: Nageswara R. Palepu; Julie A. Hutt, both of Dublin, Ohio

[73] Assignee: Erbamont, Inc., Dublin, Ohio

[21] Appl. No.: 583,896

[22] Filed: Sep. 17, 1990

Related U.S. Application Data

[63] Continuation-in-part of Ser. No. 528,290, May 22, 1990, abandoned, which is a continuation of Ser. No. 340,978, Apr. 20, 1989, abandoned.

[51] Int. Cl.$^5$ .................. A61K 31/66; C07C 229/00
[52] U.S. Cl. .................. 514/110; 514/960; 562/575
[58] Field of Search .................. 514/110, 960; 562/575

[56] References Cited

U.S. PATENT DOCUMENTS 4,537,883 8/1985 Alexander et al. .................. 514/110
4,659,699 4/1987 Francis .................. 514/53

*Primary Examiner*—Thurman K. Page
*Assistant Examiner*—G. S. Kishore
*Attorney, Agent, or Firm*—Thompson, Hine and Flory

[57] ABSTRACT

A stable rapidly dissolving lyophilized composition of cyclophosphamide and alanine is provided.

6 Claims, No Drawings

CYCLOPHOSPHAMIDE - ALANINE LYOPHILIZATES

CROSS-REFERENCE TO RELATED APPLICATIONS

This application is a continuation-in-part of U.S. application Ser. No. 528,290 filed May 22, 1990, now abandoned, which in turn is a continuation of U.S. application Ser. No. 340,978 filed Apr. 20, 1989, and abandoned.

BACKGROUND OF THE INVENTION

1. Field of the Invention

The present invention relates to a novel lyophilized composition containing cyclophosphamide and alanine as an excipient.

2. Description of Prior Art

U.S. Pat. No. 4,537,883 to Alexander et al. (Mead Johnson & Co.) discloses various lyophilizats of cyclophosphamide. These lyophilizates are prepared by lyophilizing a solution of cyclophosphamide and one or more excipients and re-hydrating the product such that it contains about 4% moisture. The patent is based upon a comparative study of lyophilizate cakes and the dissolution time for lyophilizates of cyclophosphamide prepared using a number of excipients. The study concludes that the lyophilizate prepared with mannitol gives a better cake and faster dissolution time than the lyophilizates prepared with other excipients. The patent also teaches that the lyophilized cyclophosphamide-mannitol composition exhibits better thermal stability if it contains an equimolar amount of water based on cyclophosphamide. The preferred lyophilizate contains 20 parts cyclophosphamide, 1.25 to 2 parts water and 10 to 85 parts mannitol. Among the excipients evaluated in the patent are mannitol, sodium bicarbonate, lactose, polyvinyl pyrrolidone (PVP), arginine, and tartaric acid and combinations of mannitol and various organic acids including the amino acids glycine and arginine as secondary excipients. The lyophilizates illustrated in the patent prepared with the amino acids provided poor cakes which exhibited poor dissolution times.

SUMMARY OF THE INVENTION

It has now been found that lyophilizates of cyclophosphamide having improved dissolution times and good shelf stability can be obtained using alanine as the excipient. Lyophilizates in accordance with the present invention, generally contain about 50 to 150 parts by weight of alanine per 100 parts by weight cyclophosphamide and water in the amounts discussed below. The alanine-cyclophosphamide combination is believed to be unique in that upon lyophilization it yields an anhydrous product which is crystalline whereas cyclophosphamide with other excipient combinations produced an amorphous lyophilizate.

In the present invention, as in the prior art, it is desirable to hydrate the anhydrous lyophilizate to enhance its stability. The amount of water in the lyophilizate after rehydration is preferably about equimolar to the amount of cyclophosphamide. In accordance with the invention, the crystalline anhydrous product contains between 0 and 0.5 parts water per 100 parts of cyclophosphamide and the crystalline monohydrate product contains between 5.8 and 8.2 parts water per 100 parts cyclophosphamide.

In addition to dissolving quickly, these crystalline lyophilizates generally experience less than 5% loss in potency when stored at 37° C. for a period of six weeks for the monohydrate form and less than 15% loss in potency for the anydrous form.

Accordingly, one object of the present invention is to provide a lyophilizate of cyclophosphamide using alanine as an excipient which provides a good cake which dissolves rapidly when reconstituted with water and which provides good shelf stability.

Another object of the present invention is to provide a process for preparing a lyophilizate of cyclophosphamide having a short dissoluton time and good shelf stability.

DETAILED DESCRIPTION OF THE INVENTION

Previously, as disclosed in U.S. Pat. No. 4,537,883, unsatisfactory lyophilizates have been obtained using the amino acids arginine and glycine as excipients. These lyophilizates provided poor quality cakes which were slow to dissolve. The Patent teaches that the cakes have to be hydrated to obtain adequate stability. It has now been found that lyophilizates of cyclophosphamide and alanine, an amino acid, having good shelf life and minimum dissolution time can be obtained. While cyclophosphamide-alanine lyophilizates are also hydrated to obtain the optimum storage stability, without hydration they are more stable than lyophilizates obtained with other amino acids.

Conventional lyophilization techniques can be used in the present invention including the methods described in U.S. Pat. No. 4,537,883 among other methods known to those skilled in the art. The conditions employed in the Example which follow are one example of those which can be used.

It is hypothesized that when utilizing alanine as an excipient, a crystalline product is obtained without hydration. Several amino acids were used as excipients to lyophilize cyclophosphamide. All the tested amino acids except alanine produced an amorphous lyophile. Formation of a crystalline anhydrous material during the conventional lyophilization is quite rare. Alanine is the only excipient that produced a crystalline anhydrous polymorph of cyclophosphamide.

The lyophilizate is typically prepared by lyophilizing a solution containing about 1 to 5% alanine and about 1 to 4% cyclophosphamide. The pH of the solution typically ranges between 3 and 7.

Following lyophilization, the anhydrous crystalline product is hydrated. When crystalline anhydrous cyclophosphamide is exposed to high humidity conditions (>60% RH), it picks up water rapidly (—2 hours at 80% RH) and converts into crystalline monohydrate. Hydration can be accomplished by using the conventional techniques described in U.S. Pat. No. 4,537,883 to Alexander et al. or U.S. Pat. No. 4,797,388 to Francis. The composition can also be rehydrated by aspirating water into the vial containing the lyophilizate using an ultrasonic spray nozzle which delivers a predetermined amount of water or by placing the vial in a humidity chamber having a relative humidity exceeding 85%. The hydration step according to the present invention fecilitate the phase transition of the crystalline lyophilizate from an anhydrous form to a monohydrate form. Both the crystalline anydrous and the crystalline monohydrate polymorphic forms are stable for extended period of time, with the monohydrate form being the more stable of the two.

When the lyophilizate is hydrated, it is preferred that it contains an amount of water which is about equimolar to the amount of cyclophosphamide to fully convert the lyophilizate to a crystalline monohydrate form. The lyophilized material will generally contain about 0 to 0.5 parts water and about 50 to 150 parts alanine per 100 parts of cyclophosphamide. After rehydration, the water content is increased to about 5.8 to 8.2 parts per 100 parts of cyclophosphamide. In between the range of 0.5 and 5.8 parts water per 100 parts of cyclophosphamide, the lyophilizate takes the form of an amorphous solid. The amorphous solid is unstable and can lose up to 80% of its potency when stored at 37° C. for a period of six weeks.

The effect of alanine, the concentration of the prelyophilized solution, and the water content of the lyophilizate on the stability of cyclophosphamide lyophilizates are illustrated in the following non-limiting examples.

EXAMPLE 1

Lyophilizates of cyclophosphamide and alanine were prepared as follows:

Solutions (5 ml) containing 2% (W/V) cyclophosphamide (100 mg) and 3% alanine (150 mg). The vials were frozen in a lyophilization chamber for about 12 hours at a shelf temperature of −26° C. The chamber was then evacuated to a pressure of about 100 millitorr. The samples were maintained in the chamber at a shelf temperature of 0° C. for 16 hours and 25° C. for 8 hours. After lyophilization was completed, the samples were rehydrated by placing them in an 85% humidity chamber and monitoring the weight gain. The amount of water in the lyophilizate expressed as a percent of the total composition and as a percentage of cyclophosphamide (CP) is shown in the table.

The samples were next subjected to an aging study wherein they were first assayed by HPLC, then placed in an oven at 37° C. for the periods indicated and finally re-assayed. The loss in potency expressed as a percentage loss based on the initial assay is shown in the table.

Table

| Sample No. | Excipient | % (W/V) | Water[1] | Water-CP[2] | Age (wks) | Lose in Potency |
|---|---|---|---|---|---|---|
| 1 | Alanine | 3 | 1.1 | 3.0 | 6 | 85% |
| 2 | Alanine | 3 | 3.7-4.8 | 9.6-12.5 | 6 | less than 5% |

[1] percentage of total vial
[2] percentage based on cyclophosphamide

EXAMPLE 2

Lyophilizates of cyclophosphamide and amino acids, more particularly glycine, DL-valine, DL-serine and DL-alanine were prepared using the method of Example 1. The resulting lyophilizates had good cake characteristics and dissolved quickly on reconstitution to a pH near 6. For each of the different amino acid excipients, some vials were hydrated while others were not. The samples were subjected to an aging study wherein they were assayed by HPLC after 6 weeks of storage at 37° C. All of the hydrated vials showed excellent stability. However, with respect to the vials which were not hydrated, the samples containing either glycine, DL-valine or DL-serine excipients had less than 20% of active pharmaceutical remaining, indicating that these materials needed to be hydrated to be shelf stable. The sample which utilized alanine as the excipient maintained 84% of its original amount, indicating that the non-hydrated lyophilizate could be used as shelf stable product. Six and eighteen-week stability data for samples which utilized alanine as an excipient are set forth in Table 2.

TABLE 2

| Cyclophosphamide/DL-Alanine Stability at 37° C. | | |
|---|---|---|
| Sample | Weight Gain during rehy-1 dration (mg) | Stability 37° C. |
| | | 6 wks | 18 wks |
| 94 mg cyclophosphamide/ 150 mg DL-Alanine | Not rehydrated 5.6 | 84% 102% | — 98% |

EXAMPLE 3

A lyophilizate of cyclophosphamide was produced by providing a solution containing 20mg/ml cyclophosphamide and 30mg/ml of -DL-alanine, and 5 ml of the solution was inserted into several 10 ml vials. The vials were immediately frozen at a temperature of approximately −15° C. and lyophilized according to standard procedure. The vial was tested for stability at 37° C. and assayed after 6 and 12 weeks. After 6 weeks, the vial contained 85% of the initial material. After 12 weeks, the vial contained 90% of the original material.

The results of the examples show that a cyclophosphamide lyophilizate can be produced without requiring a hydration step when alanine is utilized as an excipient. The studies further show that the non-hydrated samples are shelf stable for at least 6, and in some instances, 12 weeks at 37° C. Based upon X-ray diffraction data taken from the samples, it is hypothesized that the unexpected stability of the lyophilizates is directly attributable to the crystalline anhydrous form. The study further shows that additional shelf stability may be obtained by hydrating the lyophilizate prior to storage to convert the crystalline anhydrous form to a crystalline monohydrate form.

EXAMPLE 4

Cyclophosphamide lyophilizate samples were produced by lyophilizing 5 ml aliquots of solutions containing 33.3 mg/ml cyclophosphamide and either 17.7 mg/ml, 35.4 mg/ml or 53.1 mg/ml of L-alanine. The concentrations of L-alanine added were selected to provide samples having weight ratios of cyclophosphamide to L-alanine of approximately 1:0.5, 1:1 and 1:1.5 respectively. Two samples at each weight ratio were produced. The solutions were froze at −35° C. Drying was performed by utilizing a primary drying step at −5° for 24 hours followed by a secondary drying step at 25° C. for 8 hours. The samples were analyzed by X-ray diffraction and differential scanning calorimetry. The 1:0.5 and 1:1 lyophilizates were determined to be crystalline anhydrous solids whereas the 1:1.5 lyophilizates were determined to be an amorphous solid. The materials were stored at 37° C. for two months, and the samples were then analyzed for stability. The 1:0.5 samples had an average of 92% material remaining and the 1:1 samples had an average of 90% material remaining. One vial of the 1:1.5 sample contained 90% of its original material while the other vial contained 18% of its original material.

Having described the invention in detail and by reference to preferred embodiments thereof, it will be apparent that modifications and variations ere possible without departing from the scope of the invention defined in the appended claims.

What is claimed is:

1. A lyophilized cyclophosphamide composition comprising cyclophosphamide, alanine and water wherein the amount of water ranges from approximately 0 parts to about 0.5 parts or from about 5.8 parts to about 8.2 parts per 100 parts by weight of cyclophosphamide, and wherein the amount of alanine is present in amount of about 50 to 150 parts per 100 parts by weight of cyclophosphamide.

2. The composition of claim 1 wherein said composition is produced by lyophilizing a solution of cyclophosphamide containing about 1.7% to 5% by weight of analine and having a pH of 3.0 to 7.0.

3. A lyophilizate of crystalline anhydrous cyclophosphamide containing about 0 parts to about 0.5 parts by weight of water and about 50 to 150 parts alanine per 100 parts by weight of cyclophosphamide.

4. The lyophilizate of claim 3 wherein said lyophilizate is prepared by lyophilizing a solution containing about 1 to 5% alanine and having a pH of about 3.0 to 7.0.

5. A lyophilizate of crystalline monohydrate cyclophosphamide containing about 5.8 to 8.2 parts by weight water and about 50 to 150 parts alanine per 100 parts cyclophosphamide.

6. The lyophilizate of claim 5 wherein said lyophilizate is prepared by lyophilizing a solution containing about 1 to 5% alanine and having a pH of about 3.0 to 7.0 and hydrating the product.

* * * * *